United States Patent
Mirza (10) Patent No.: US 6,358,251 B1
(45) Date of Patent: Mar. 19, 2002

(54) METHOD AND APPARATUS FOR FORMING A CAVITY IN SOFT TISSUE OR BONE

(75) Inventor: Sohail Mirza, Bellevue, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 09/532,511

(22) Filed: Mar. 21, 2000

(51) Int. Cl.$^7$ ................................................ A61B 17/32

(52) U.S. Cl. ............................ 606/79; 606/172; 606/96

(58) Field of Search ............................. 606/79, 80, 81, 606/83, 84, 96, 97, 98, 167, 170, 171, 172, 178, 180

(56) References Cited

U.S. PATENT DOCUMENTS

| 5,192,293 A | * | 3/1993 | Cartwright et al. | ......... 606/172 |
| 5,242,461 A | * | 9/1993 | Kortenbach et al. | ........ 606/159 |
| 5,928,239 A | * | 7/1999 | Mirza | ......................... 606/79 |

* cited by examiner

Primary Examiner—John J. Wilson
Assistant Examiner—Melba Bumgarner
(74) Attorney, Agent, or Firm—Delbert J. Barnard; Joan H. Pauly (57) ABSTRACT

A first stop member (74) is connected to and extends upwardly, perpendicular to a longitudinal frame member (72). A second stop member (80) is connected to and projects upwardly and perpendicular to a base member (82). The base member (82) is supported by and is guided along the frame member (72) by a longitudinal rib (84) on the frame member (72) and a longitudinal recess (86) formed in the bottom of the base member (82). The stop members (74, 80) include shaft receiving openings (78, 120). A forward portion of a rotary shaft (12) projects forwardly through the opening (78) in the forward stop member (74) and then projects forwardly through a guide passageway in a guide member (52) having a forward end surface (53). A rear portion of the shaft (12) projects through opening (120) in the rear stop member (80). The shaft (12) includes an abutment (46) that is positioned between the two stop members (74, 80). The cutting tip member (14) is pivotally connected to the forward end of the shaft (12). In use, the cutting tip member (14) is oriented to be coaxial with the shaft (12) and is moved into a percutaneous access opening formed in a body part ( ). The shaft (12) and the cutting tip member (14) are rotated relative to the stop members (74, 80). This causes the cutting tip member (14) to swing outwardly and cut a cavity in the body material that has a radius greater than the radius of the shaft (12). Forward movement of the shaft (12), to move the abutment (46) against the forward stop member (74) moves the cutting tip member (14) to the location of a desired forward boundary of the cavity. Movement of the shaft (12) rearwardly to move the abutment (46) into contact with the rear stop member (80) moves the cutting tip member (14) to the location of a desired second end boundary of the cavity.

24 Claims, 8 Drawing Sheets

METHOD AND APPARATUS FOR FORMING A CAVITY IN SOFT TISSUE OR BONE

TECHNICAL FIELD

This invention relates to a method and apparatus for forming a cavity in soft tissue or bone in a minimally invasive manner. More particularly, it relates to a rotary cutting bit that may be inserted percutaneously, such as through a needle or cannula, and then expanded in diameter upon rotation to form an internal cavity having a radius many times that of the insertion opening, and to structure and steps for controlling the location of one or both of the ends of the cavity that is being formed.

BACKGROUND OF THE INVENTION

The Background of the Invention in my U.S. Pat. No. 5,928,239, granted Jul. 27, 1999, and entitled Percutaneous Surgical Cavitation Device And Method is hereby made a part of this Background of the Invention.

My U.S. Pat. No. 5,928,239 discloses a rotating cutting tool for forming a cavity inside a body region. The cutting tool is inserted through a small diameter access opening into the body region where the cavity is to be formed. The cutting tool is moved forwardly to where the forward end boundary of the cavity is to be formed. Then, the cutting bit is rotated and is sometimes pulled rearwardly to lengthen the cavity. Eventually, a rearward end boundary is formed.

As explained in my U.S. Pat. No. 5,928,239, more than one cutting tip member can be used for forming a given cavity. For example, a first cutting tip member of a predetermined length can be used for cutting a substantially semi-cylindrical first end portion of the cavity. Then, a second cutting bit having a shorter cutting tip member may be substituted for the first cutting bit and then rotated for cutting a central portion of the cavity that is smaller in diameter than the first end portion. Then, the second cutting bit can be replaced by the first cutting bit and the first cutting bit can be used to form a substantially semi-spherical second end portion for the cavity. Or, as also disclosed in my U.S. Pat. No. 5,928,239, a single size cutting bit can be used to form the entire cavity. In either case, cutting is started at a first end boundary of the cavity and is continued on to a second, opposite end boundary of the cavity. Rotation is started with the cutting tip member positioned to cut the first end boundary. Then, the cutting bit may be moved axially while it is being rotated so as to lengthen the cavity. The endwise movement of the cutting tool is continued until the cutting tip member is positioned at the second, opposite end boundary of the cavity.

There is a need for an apparatus and method for accurately establishing one or both end boundaries of the cavity and for preventing unwanted cutting beyond the boundary or boundaries. It is an object of the present invention to provide such an apparatus and method.

BRIEF SUMMARY OF THE INVENTION

According to the present invention, a cavity cutting bit is provided that has an elongated shaft that includes a forward end, a cutting tip member that includes a cutting end and a mounting end, and a hinge that pivotally connects the mounting end of the cutting tip member to the forward end of the shaft. The cutting tip member is mounted on the forward end of the shaft for free swinging relative to the shaft between a position in which the cutting tip member is coaxial with the shaft and a position in which the cutting tip member extends at an angle from the shaft. The cutting bit is inserted, cutting tip member first, into a small diameter opening or passageway that leads into the interior of a body part. At this time, the cutting tip member is coaxial with the elongated shaft. When properly located within the body part, the cutting bit is rotated. In response to this rotation, the cutting tip member swings outwardly and acquires a cutting or fly diameter that is substantially larger than the small opening through which it and the shaft were inserted.

According to an aspect of the invention, the apparatus is provided with a cutting bit guide member having a forward end portion that is adapted to be placed against an outer surface region of a body part and a guide passageway that is adapted to receive the cutting tip member and the shaft, in that order. An abutment is provided on the shaft at a predetermined distance rearwardly from the cutting tip member. The apparatus includes an axial movement stop for the shaft having a stop surface that is at a predetermined fixed position relative to both the forward end portion of the guide member and the abutment on the shaft. In use, the forward end portion of the guide member is placed against the outer surface region of the body part. Then the cutting tip member and the shaft are inserted into the guide passageway and are moved into the body part to where a cavity is to be formed. The shaft is allowed to be moved endwise until the abutment on it is against the stop surface. The shaft is rotated to cause the cutting tip member to swing outwardly and form the cavity. Movement of the abutment against the stop surface prevents further endwise movement of the cutting tip member and establishes a predetermined first end boundary for the cavity.

According to another aspect of the invention, the guide member is adjustable in length for changing the distance between the forward end surface of the guide member and the stop surface.

According to a further aspect of the invention, the apparatus is provided with two axial movement stops, each having a stop surface that confronts the other stop surface. The abutment on the shaft is located between the two stop surfaces. Movement of the abutment against one of the stop surfaces establishes a first end boundary for the cavity that is formed during rotation of the cutting bit. Movement of the abutment against the other stop surface establishes a second, opposite end boundary for the cavity.

According to yet another aspect of the invention, either one or both of the movement stops is adjustable in position relative to the other movement stop, for changing the distance between the two stop surfaces and for changing the positions of the two stop surfaces relative to the forward end surface of the guide member.

In the preferred embodiment, the first motion stop extends upwardly from and substantially perpendicular to an elongated base member and the guide member extends forwardly from the first motion stop. Preferably also, the guide member is adjustable in length for adjusting the position of its forward end surface relative to the stop surface on the motion stop member.

A method aspect of the invention includes the step of providing a percutaneous access opening into a body part in which a cavity is to be formed. Providing a stop member spaced outwardly from the access opening and providing said stop member with a shaft receiving opening. Inserting through the shaft opening and then through the access opening a rotary cavitation device comprising (i) an elongated shaft having a radius and an axis of rotation, (ii) a cutting tip member having a fixed length; (iii) a hinge interconnecting the shaft and the cutting tip member and allowing a free swinging movement of the cutting tip member between a position in which the cutting tip member is coaxial with the shaft and a second position in which the cutting tip member extends outwardly at an angle from the shaft; and (iv) an abutment on the shaft rearwardly of the stop member. The shaft abutment and the stop member are positioned such that when the shaft is moved axially forwardly to place the abutment into contact with the stop member, the cutting tip member is positioned at an end boundary of the internal cavity that is to be formed in the body part. Then, the shaft is rotated at a velocity sufficient to cause the cutting tip member to swing from its first position into its second position. The cutting tip member is moved as necessary to form the desired internal cavity in the body part and provide such cavity with a radius that is greater than the radius of the shaft. Thereafter, the shaft and the cutting tip member are withdrawn from the access opening.

A further aspect of the invention involves providing a second stop member that is spaced outwardly from the abutment on the shaft. This positions the abutment between the two stop members. The second stop member is positioned at such a location that when the shaft is retracted to move the abutment into contact with the second stop member, the cutting tip member is at a second, opposite end boundary of the cavity that is being formed.

In preferred form, the forward stop member is provided with a forwardly projecting guide tube having a front end surface that is positionable against a surface portion of the body part that is outwardly of where the cavity is to be formed. The guide tube is provided with a passageway for the rotary cavitation device that is in alignment with the shaft receiving opening in the stop member. The cutting tip member of the rotary cavitation device is inserted forwardly into and through the guide passageway and into and through the access opening into the body part and is then rotated to form the cavity.

According to yet another aspect of the invention, the shaft abutment and the stop member can be positioned by adjusting the length of the guide tube.

The second stop member may be mounted on a longitudinal base member that includes lead screw thread. This base member is positioned on a longitudinal frame member that is connected to the first stop member. An adjustment ring is provided that surrounds the base member and the frame member and includes internal threads that engage the lead screw threads on the base member. The ring is rotated for causing movement of the base member and the second stop member relatively along the frame member for purposes of positioning the second stop member.

Other objects, advantages and features of the invention will become apparent from the description of the best mode set forth below, from the drawings, from the claims and from the principles that are embodied in the specific structures that are illustrated and described.

BRIEF DESCRIPTION OF THE SEVERAL VIEWS OF THE DRAWING

Like reference numerals are used to designate like parts throughout the several views of the drawing, and.

DETAILED DESCRIPTION OF THE INVENTION

FIGS. 1–7 of the drawing are identical to FIGS. 1–7 of the drawing in the aforementioned U.S. Pat. No. 5,928,239. These drawing figures show a cavity forming tool or bit 10 composed of an elongated shaft 12 and a cutting tip member 14 that is pivotally connected to the shaft 12. Shaft 12 and cutting tip member 14 are cylindrical and are substantially equal in diameter. The cutting tip member 14 has a forward end cutting portion and a rear end mounting portion that is pivotally connected to a forward end portion of the shaft 12. As illustrated, the forward end portion of the shaft 12 is provided with a slot 18 that divides the forward end portion of the shaft 18 into a pair of tines. The mounting end portion 20 of the cutting tip member 14 has a single central tine 20 that fits into the slot 18. A pivot pin 22 extends through the three tines and forms the pivot joint. The pivot pin receiving openings in the shaft 12 may be sized to snugly receive the ends of the pivot pin 22. The pivot pin receiving opening in the tine 20 may be slightly larger so that the cutting tip member 14 can rotate freely about the pivot pin 22.

As previously stated, the shaft 12 and the cutting tip members are cylindrical. The cutting of the slot 18 into the cylindrical end portion of shaft 12 leaves two tines, one on each side of the slot 18. Each tine is a segment of a cylinder having a flat inside surface and a cylindrical outside surface. The ends of the tines are rounded at 24. The rear end portion of cutting tip member 14 is cut away on both of its sides to form the tine 20. Its inner end is also rounded, as shown in FIGS. 1–4. When the tine 20 is within the slot 18, the two forwardly directed tines of the shaft 12 and the rearwardly directed tine 20 of the cutting bit member 14 provide the joint region with a substantially cylindrical shape substantially matching the cylindrical shapes of the shaft 12 in the cutting tip member 14.

Preferably, the shaft 12 and the cutting tip member 14 are made from the same material. The particular material and the hardness of the material is dependent on the particular body material that will be cut to form the cavity. Typically, the shaft 12 and the cutting tip portion 14 are made from stainless steel or titanium. The formation of a cavity in a hard bone would require the use of a harder material than is required for forming a cavity in a soft tissue such as a brain or a liver.

In the illustrated embodiment, the cutting tip member 14 is adapted by the pivot pin connection to be freely movable between a first position in which it is coaxial with the shaft 12 (FIGS. 1, 2 and 7) and a second position in which it extends generally perpendicular (FIGS. 3–6) or at some other selected angle relative to the shaft 12. It is within the scope of the present invention to pivotally connect the cutting tip member 14 on the shaft 12 for pivotal movement between the coaxial position with the shaft 12 and a second position which extends at an oblique angle rather than perpendicular to the shaft 12.

Figure 1:
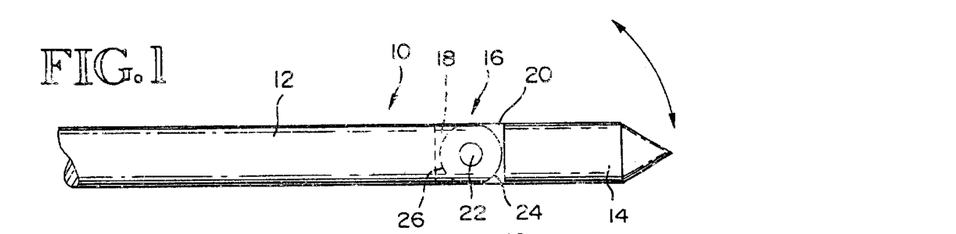
FIG. 1 is a side view of a cutting end portion of a cavity cutting bit that is a part of the apparatus of the present invention, such view showing a cutting tip member in axial alignment with a shaft to which it is pivotally connected.
Figure 2:
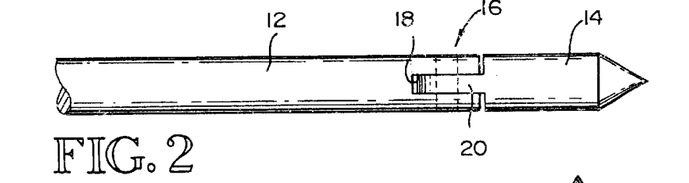
FIG. 2 is a view like FIG. 1 looking either upwardly or downwardly on the FIG. 1 position of the cavity cutting bit.
Figures 3, 4:
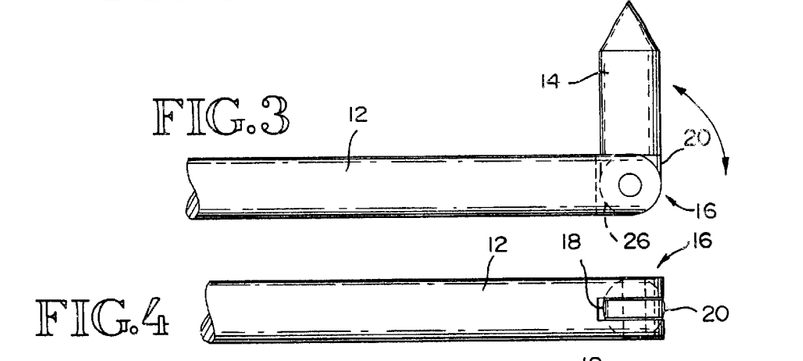
FIG. 3 is a view like FIG. 1 but showing the cutting tip member swung upwardly ninety degrees relative to the shaft.
FIG. 4 is a view looking upwardly at the cutting bit with its cutting tip member in the position of FIG. 3.
Figure 5:
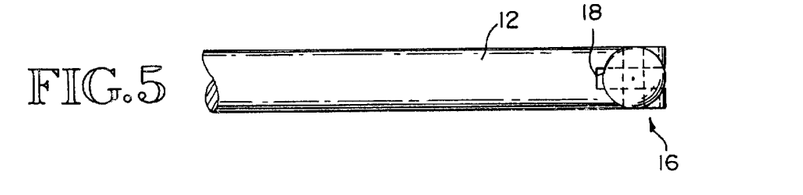
FIG. 5 is a view looking downwardly on the bit with its cutting tip member in the position of FIG. 3.
Figure 6:
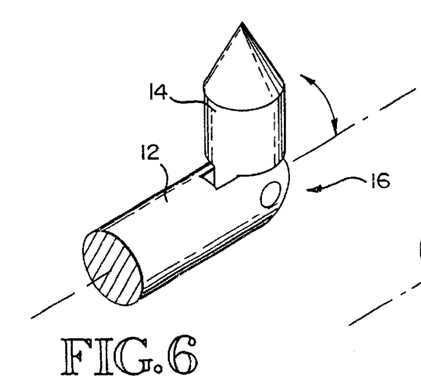
FIG. 6 is a pictorial view of the cavity cutting bit when it is in the position shown by FIG. 3.
Figure 7:
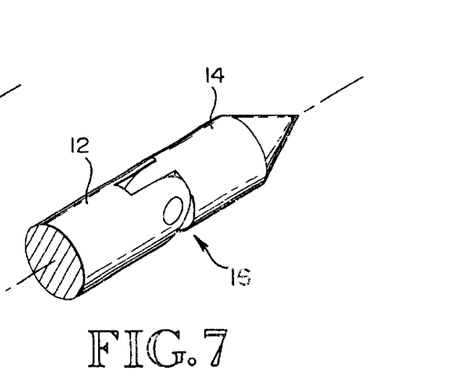
FIG. 7 is a pictorial view of the cavity cutting bit when it is in the position shown by FIGS. 1 and 2.
Figure 8:
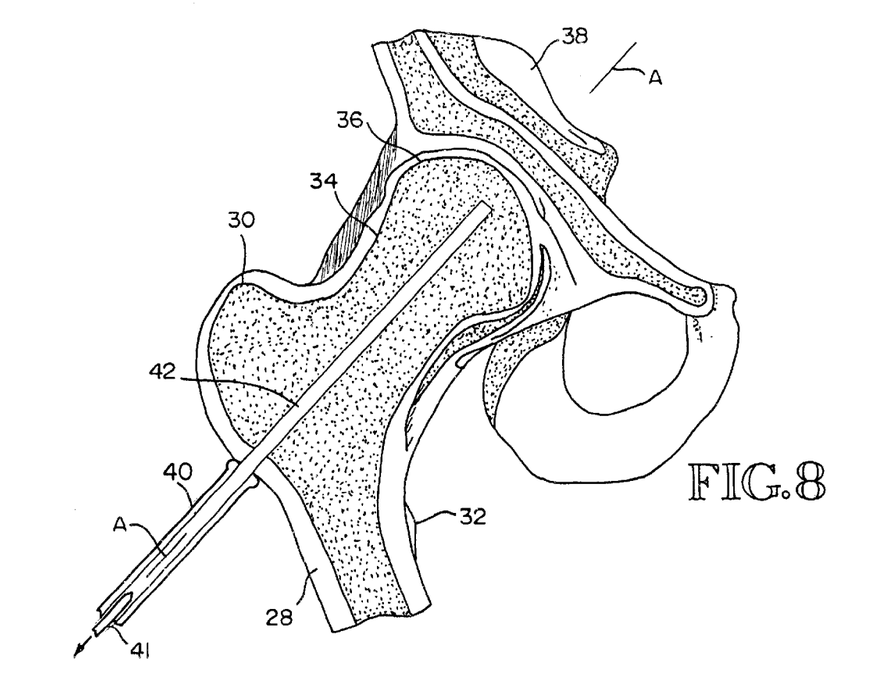
FIG. 8 is a sectional view through a femur region of a human hip joint showing a guide tube positioned to guide an orthopedic drill bit for drilling a pilot hole, such view showing a pilot hole.
Figure 9:
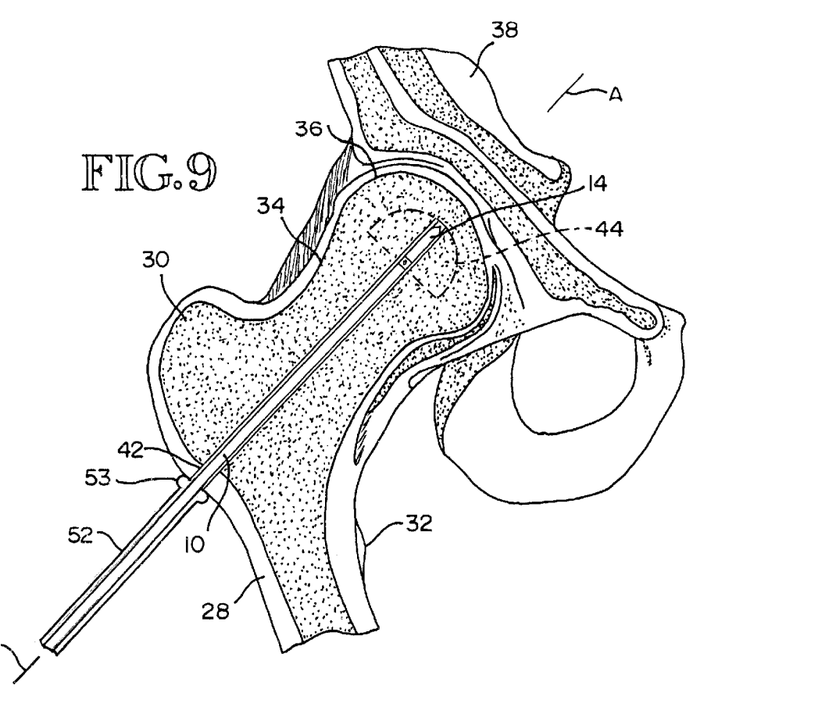
FIG. 9 is a view like FIG. 8 but showing a new guide tube that contacts the body where it surrounds the pilot hole and showing the cavity cutting bit inserted into the new guide tube.

FIGS. 8 and 9 are similar to FIGS. 8 and 9 is U.S. Pat. No. 5,928,239. These views are sectional views through the right hip joint of a human body. The illustrated parts include the right femur 28, the greater trochanter 30, the lesser trochanter 32, the neck 34, the head 36 and the ilium 38. As shown by FIG. 8, a guide tube 40 is positioned with its inner end against the tissue outwardly of the body part. The path A—A of the guide tube 40 may be determined by use of preoperative imaging or active fluoroscopy performed during the procedure. An orthopedic drill bit 41 is inserted into the guide tube 40 and used to form a pilot hole 42 that is sized to receive the cavity forming tool 12, 14. In FIG. 8, a tip portion of the drill bit 41 is shown being withdrawn from the guide tube 40.

Figure 10:
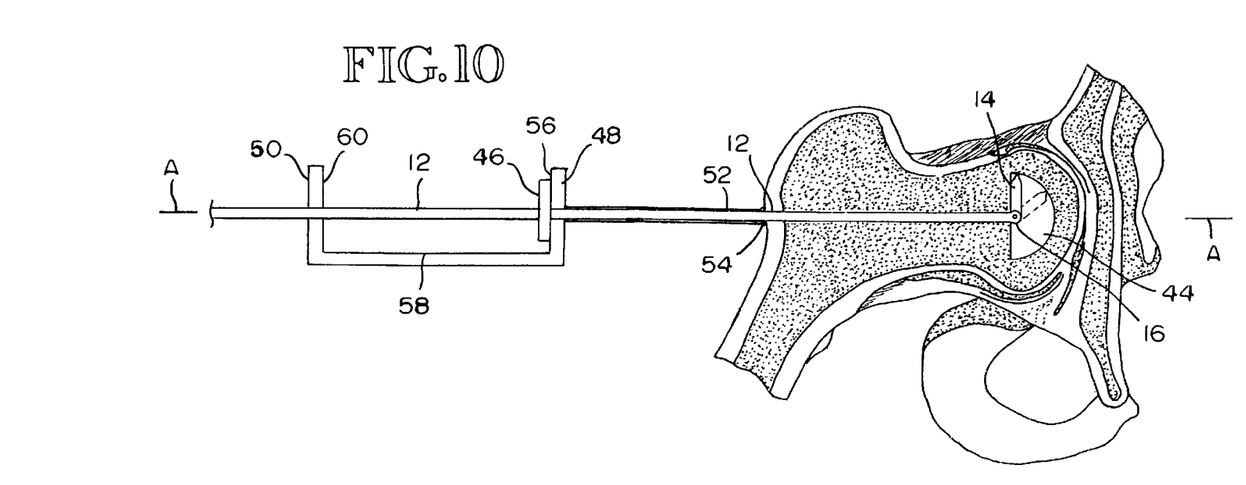
FIG. 10 is a view like FIG. 9, but showing the cutting bit being rotated to form a cavity, and further showing schematically an apparatus of the invention that limits forward movement of the cutting bit into the body material in which the cavity is being formed.
Figure 11:
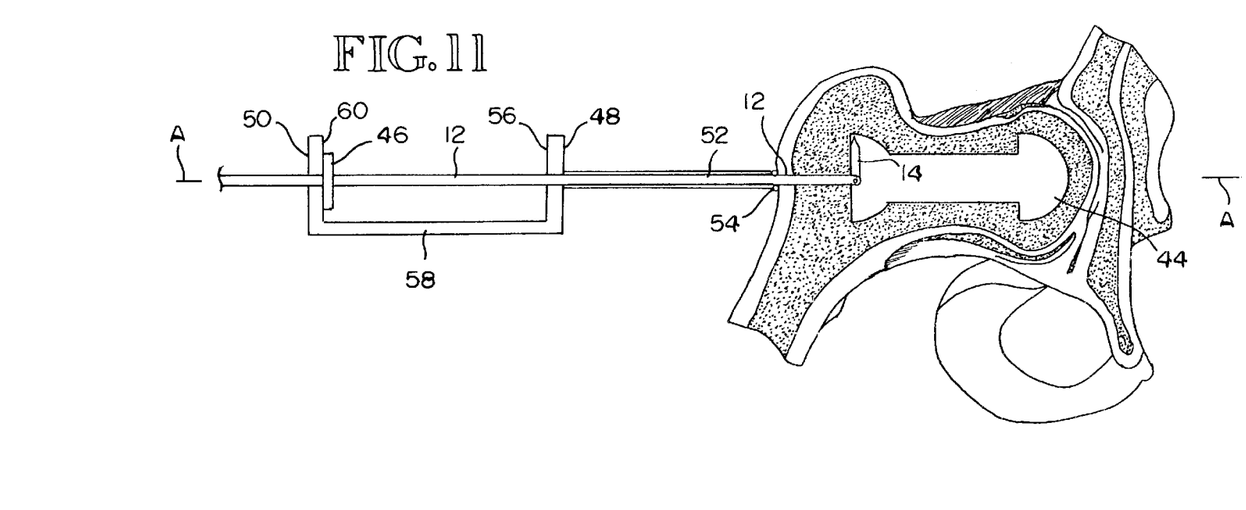
FIG. 11 is a view like FIG. 10 but showing the cavity cutting bit being used to form a second enlarged end portion for the cavity and schematically showing an apparatus of the invention that limits rearward movement of the cutting bit into the body material in which the cavity is being formed.

FIGS. 10 and 11 show the same body part region as FIGS. 8 and 9. They also show the same cutting tool that is shown in FIGS. 1–7 in combination with schematic diagrams of the cutting bit guide and control apparatus of the present invention.

According to an aspect of the invention, the shaft 12 is provided with at least one abutment 46 that is positionable between two axially spaced apart stop members 48, 50. The forward stop member 48 is connected to the rear end of the guide tube 52. The forward end of guide tube 52 is designated 54. It is adapted to fit against an outer surface region of the body part where it surrounds the entrance to the pilot hole 42. Guide tube 52 has an inner diameter that is slightly larger than the outer diameters of the shaft 12 and the cutting tip member 14. Stop member 48 includes a stop surface 56 (FIG. 11) that extends perpendicular to the guide tube 52. Stop member 50 also extends perpendicular to the guide tube 52. A base member 58 connects the two stop members 48, 50 together.

Figures 12, 13:
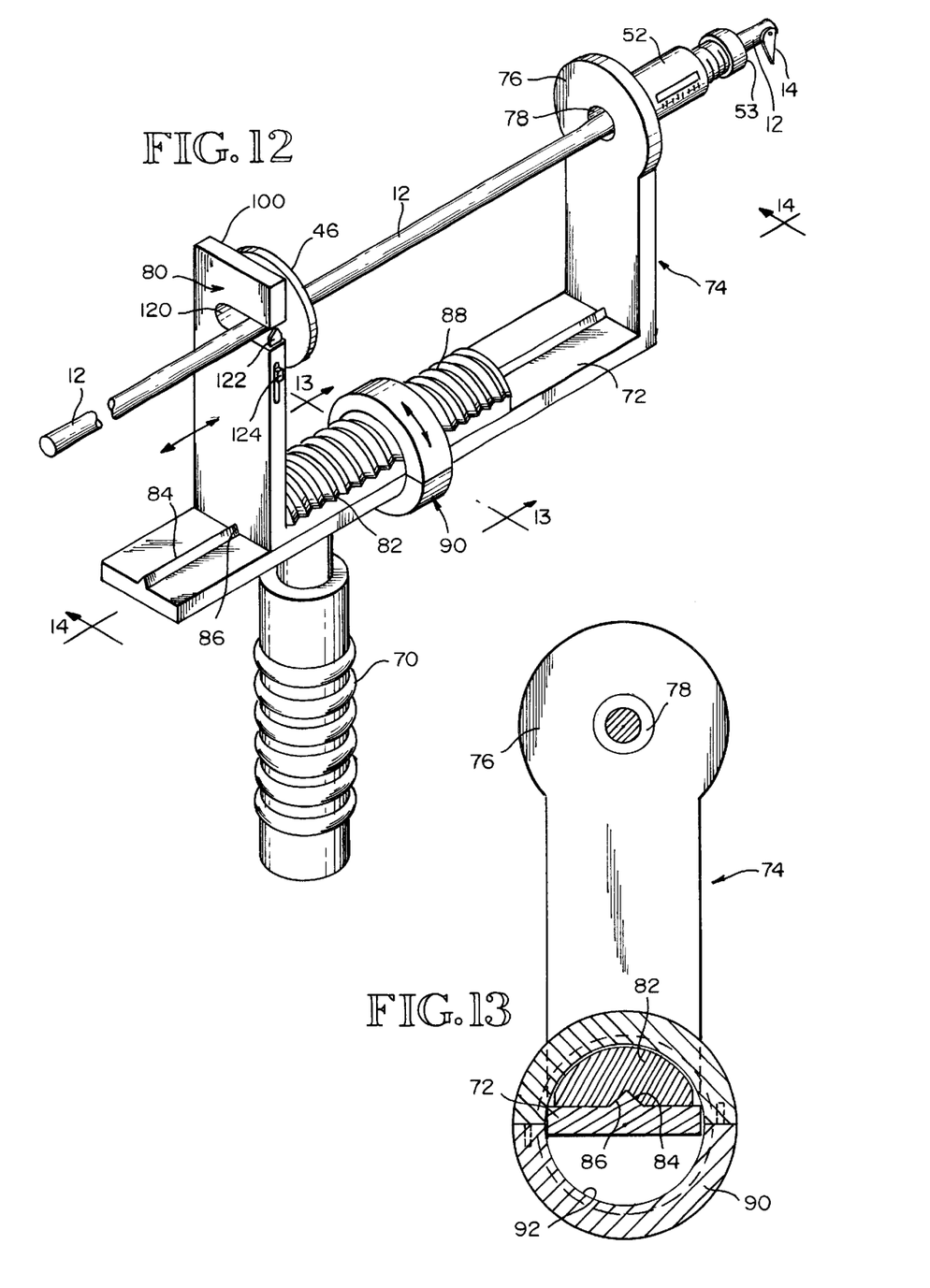
FIG. 12 is a pictorial view of a preferred embodiment of the apparatus of the present invention, such view looking downwardly onto the apparatus and towards its rear end and one side.
FIG. 13 is a cross sectional view taken substantially along line 13—13 of FIG. 12.

It is desirable to make the forward end surface 54 of the guide tube 52 adjustable in position lengthwise of the guide tube 52 relative to the stop surfaces 56, 60. It is also desirable to make the distance between the two stop surfaces 56, 60 adjustable. The first adjustment can be made by making the guide tube 52 adjustable in length. The second adjustment can be made by making the stop member 50 adjustable in position relative to the stop member 48. An embodiment of the invention utilizing these adjustments will now be described with reference to FIGS. 12–16. FIGS. 12–16 show a device having a handle 70 that is connected at its upper end to a longitudinal frame member 72. A first motion stop member 74 is connected to and extends upwardly from and perpendicular to the frame member 72. Motion stop member 74 includes a stop surface 76 and a guide opening 78 for receiving the shaft 12 and the cutting bit member 14. As shown in FIGS. 10 and 11, the shaft 12 is formed to include an abutment 46 shown in the form of a disc. A second motion stop member 80 projects upwardly from a base member 82 that sets down on the frame member 72. As best shown by FIG. 13, the frame member 72 includes an upwardly projecting guide rail 84 that extends lengthwise of the frame member 72 and fits into a longitudinal guide slot 86 formed in the bottom of base 82. Base member 82 is slidable lengthwise back and forth along frame member 72 along a definite path established by the rib 84 and the groove 86. Motion stop member 80 extends upwardly substantially perpendicular to base 82. Stop member 80 is also substantially parallel to stop member 74.

Figure 14:
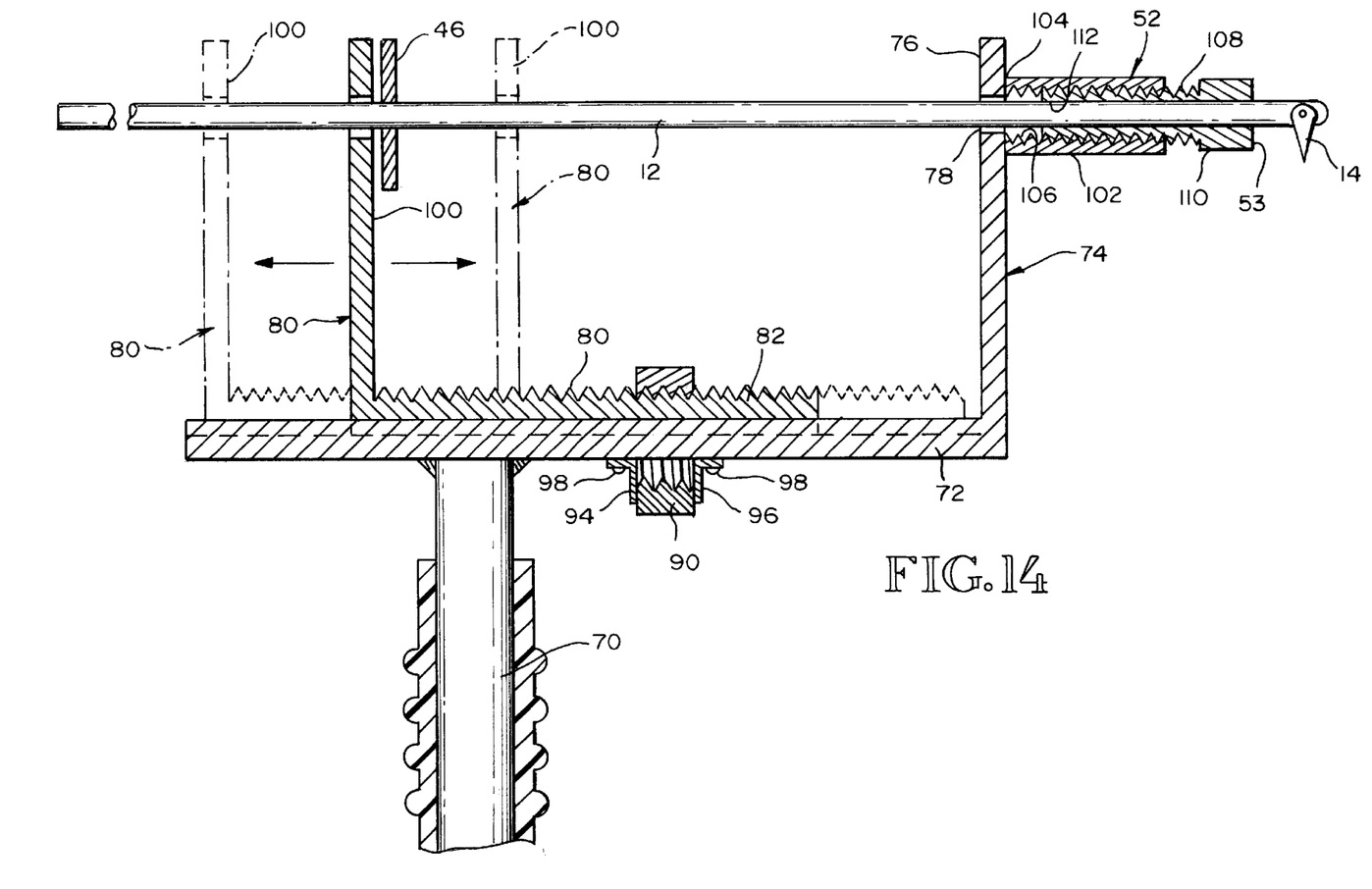
FIG. 14 is a longitudinal sectional view taken substantially along line 14—14 of FIG. 12, such view showing a rear stop member in a position with its threaded base projecting forwardly.
Figure 15:
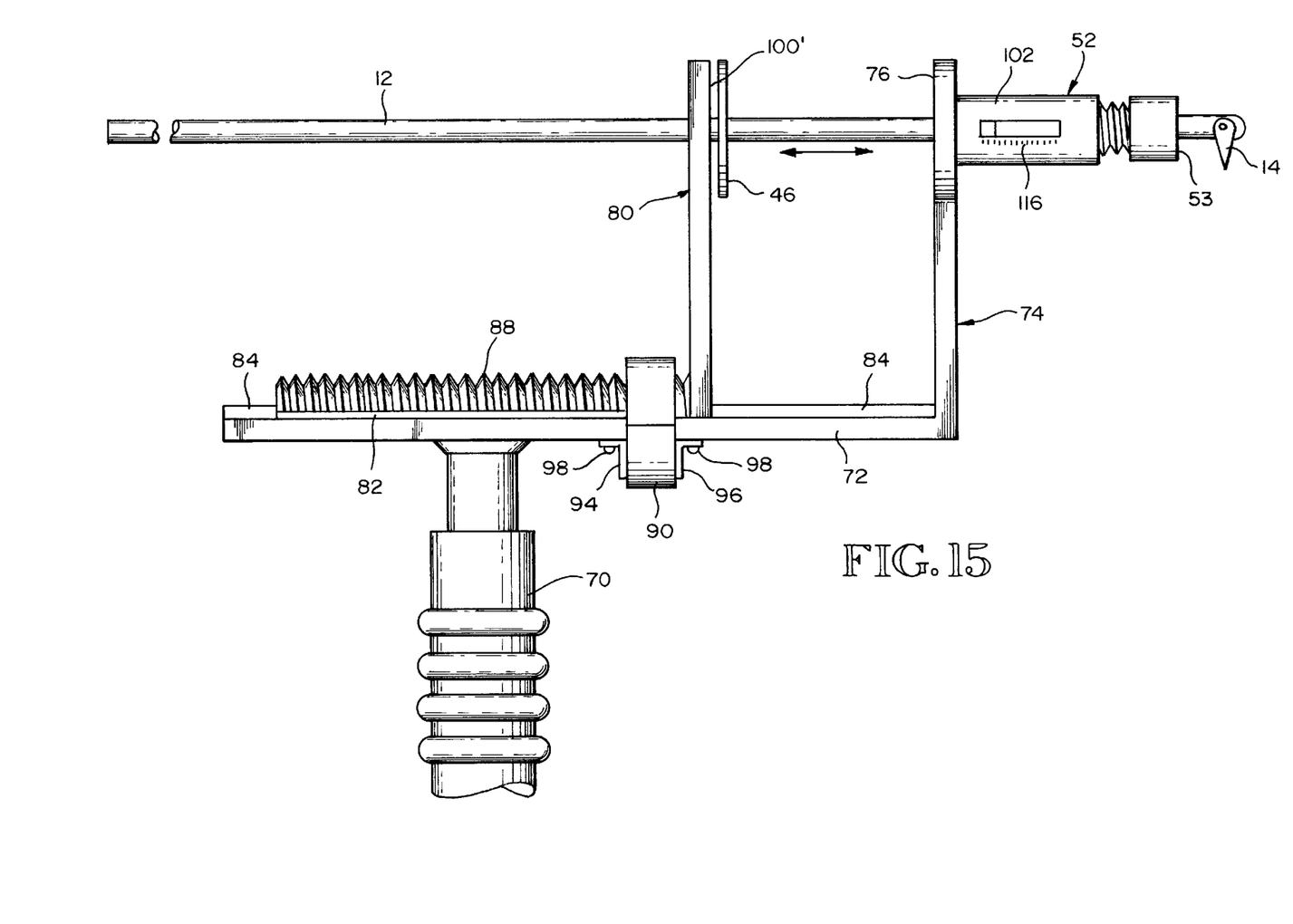
FIG. 15 is a view like FIG. 14, but showing the threaded base of the rear stop member projecting rearward.
Figure 16:
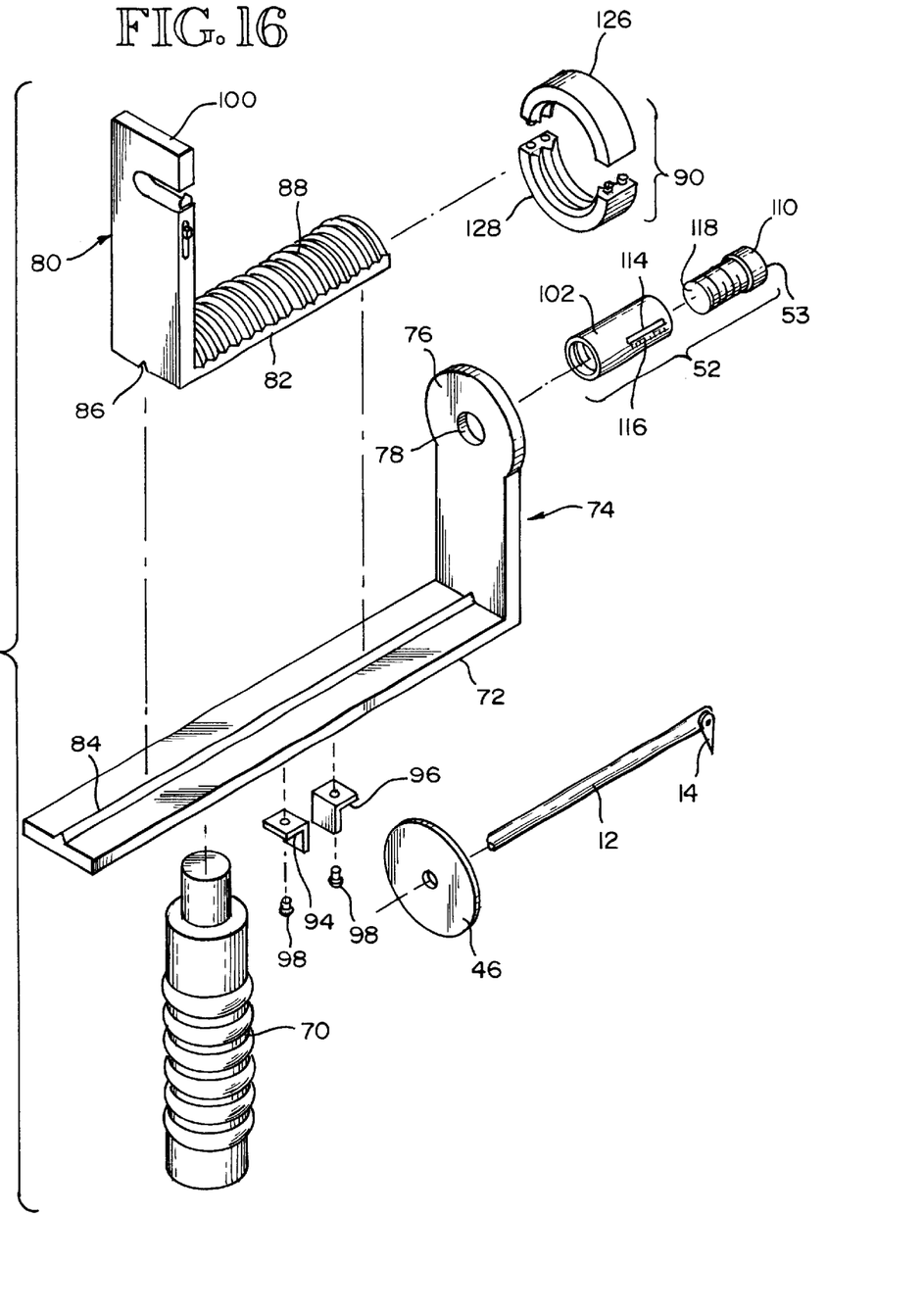
FIG. 16 is an exploded pictorial view of the apparatus of FIGS. 12–15, taken from the aspect of FIG. 12.

The upper portion of the base member 82 is in the form of a helical screw segment 88. As best shown by FIG. 13, an adjustment ring 90 surrounds both the frame member 72 and the base member 82. Ring 90 includes internal threads 92 which mesh with the external threads on screw segment 88. As shown by FIGS. 14–16, the ring 90 is trapped axially between a pair of retainers 94, 96 that may be connected by screws 98 to the bottom of frame member 72. Ring 90 is rotatable in position about the members 72, 82 but is restrained against movement lengthwise along frame member 72. As a result, rotation of ring 90 will cause the base member 82 to move one way or the other lengthwise of frame member 72, depending on the direction of rotation of the ring 90. When the ring 90 is rotated in one direction, it moves the second stop member 80 away from the first stop member 74. When ring 90 is rotated in the opposite direction it moves the second stop member 80 towards the first stop member 74. In this manner, the stop surfaces 76, 100 can be moved together and apart.

In the embodiment of FIGS. 12–16, the guide tube 52 is adjustable in length. It comprises an internally threaded, tubular rear portion 102 that is at its rear end 104 welded or otherwise connected to the movement stop member 76. The internal threads 106 engage external threads 108 on a tubular forward member 110. Member 110 includes a center passageway 112 that is sized to receive and guide the shaft 12. The forward end of member 110 provides the forward end surface of the guide tube 52. As shown by FIGS. 12, 15 and 16, the sidewall of the tubular member 102 may include a longitudinal slot 114 that is bordered by gauge marks 116. The position of the inner end 118 of member 110 relative to a gauge mark 16 will identify the axial distance of the end surface 53 from the stop surface 76. Thus, the two members 102, 110 are like the gauge elements in a micrometer.

The rear movement stop member 80 may include a slot 120 that is open at its outer end and closed at its inner end. The open outer end may be provided with a slide lock having a closure member 122 and a control member 124 that are really one member that is slidably mounted on the member 80 for movement between an upper position, shown in FIG. 12, in which the closure member 122 closes the open end of the slot 120, and a down position in which the closure member 122 is moved clear of the slot opening. The user moves the member 122, 124 by placing a thumb or fingertip on the control member 124 and then moving it either upwardly or downwardly. When the latch member 122 is in its open position, and the member 80, 82 is in a rearward position, the cutting tip member 14 is swung up into a position in which it is coaxial with the shaft 12. Cutting tip member 14 is then aligned with opening 78 and is then moved forwardly through opening 78 and through the interior of the guide member 52. Then, the member 80, 82 is moved forwardly so as to place the rear portion of shaft 12 within the slot 122. Then, the slide bar 122, 124 is moved upwardly to move the closure portion 122 across the entrance of the slot 120, into the position shown by FIG. 12. As will be apparent, rotation of the adjustment ring or nut 90 will cause the threaded portion 88 of member 82 to move lengthwise through the ring 90 either towards or away from the movement stop member 74, dependent on the direction of rotation of the ring 90. As the threaded portion 88 of member 82 moves through the ring 90, the rear movement stop member 80 moves either towards or away from the forward movement stop member 74, again dependent on the direction of rotation of the ring 90. Thus, rotation of forward portion 110 of guide tube 52 relative to the rear portion 102 of guide tube 52 provides a way of adjusting the distance of the forward end surface 53 of the guide tube 52 relative to the two stop surfaces 76, 80. Rotation of the adjustment ring 90 provides a way of moving and thus adjusting the position of the stop surface 100 relative to the stop surface 76 and the forward end surface 53 of the guide tube 52.

FIG. 15 shows another way of adjusting the difference between stop surface 100 and stop surface 76. The member 80, 82 is turned around so that its lower base portion 82 projects rearwardly instead of forwardly. This places the movement stop member 80 much closer to the movement stop member 74. It also results in the surface 100' becoming the rear stop surface (FIG. 15).

In FIGS. 12, 15 and 16, the control ring 90 is shown to be constructed into two parts 126, 128 that are each in the nature of one half of a ring, i.e. they are each generally semi-cylindrical. This enables the member 80, 82 to be set down onto the longitudinal frame member, before ring member 90 is installed. It is installed by bringing the two halves 12, 128 together, one from above the threaded portion 88 of member 82 and the other from below the member 72. The two members 126, 128 are then suitably connected together to form the ring 90. This is done either before or after the members 94, 96 are attached to member 72 by the screws 98.

Alternatively, a one piece ring can be used and the handle 70 can be made to be detachable from member 72. For example, a screw joint can be provided at the upper end of handle 70, between it and the longitudinal frame member 72. With the handle 70 and the members 94, 96 removed, the member 80, 82 is installed on the member 72 and the ring 90 is installed upon the members 72, 82. When member 82 is directed forwardly, the ring 90 can first be slid endwise on the member 72 into a forward position. Then, the member 80, 82 can be set down onto the member 72. Then, the ring 90 can be moved rearwardly and threaded onto the threaded portion 80 until it is in the space that will be between the members 94, 96. Then, the members 94, 96 will be installed so as to permit rotation of ring 90 but restrain it from any axial movement along the members 72, 82. If the member 82 is to be positioned to where it projects rearwardly, as shown by FIG. 15, it can be placed down onto the member 72 and then the ring 90 can be installed and rotated to move it in position along the threaded portion 88 until it is in the region that will be between the two members 94, 96. Then, the members 94, 96 can be installed and the handle 70 can be installed.

Figure 17:
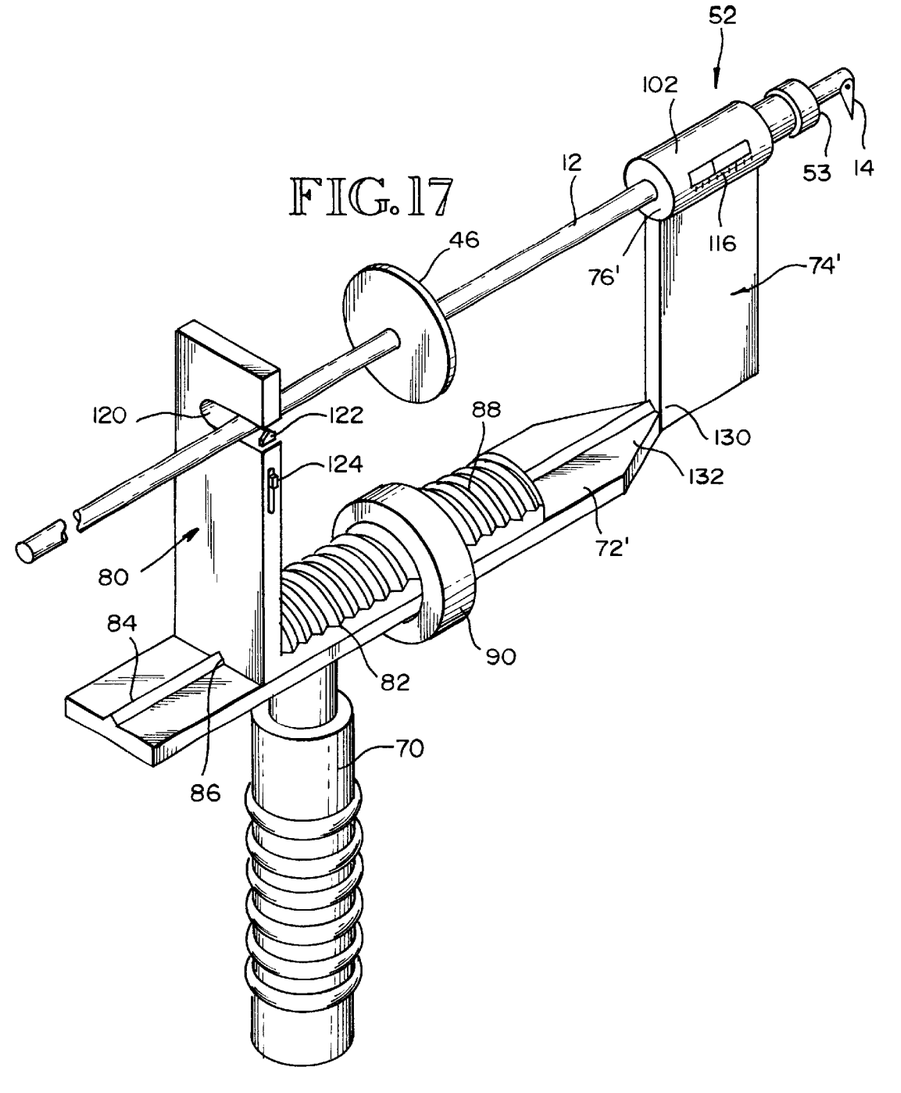
FIG. 17 is a view like FIG. 12, but showing a modified construction of the front end portion of the apparatus.

FIG. 17 shows a modified construction of the tool. It is basically like the tool that is shown by FIGS. 12–16. The difference is in the orientation of the forward movement stop 74' and its relationship to the tubular outer member 102 of the adjustable guide tube 52. In the FIG. 17 embodiment, the forward movement stop member 74 is in a plane that extends lengthwise rather than crosswise of the axis of the cutting bit. It has a front to rear dimension that is approximately equal to the length of the tubular member 102. The tubular member 102 is attached to the upper end of member 74'. A rearward lower end portion 130 of the member 74' is attached to the forward end portion 132 of the member 72'. In this embodiment, the forward end portion 132 of the member 72' may have forwardly converging side boundaries, as illustrated in FIG. 17. In other respects, the apparatus is like the apparatus shown by FIGS. 12–16.

The technique of forming the pilot hole into the internal region of a body part where a cavity is to be formed, the use of the cutting bit to form a variety of different shaped cavities in difference body parts, and various uses of the cavities are described in some detail in my aforementioned U.S. Pat. No. 5,928,239. This patent is thus hereby incorporated herein by this specific reference. The present invention includes the apparatus and method that is described herein with reference to the drawing figures in combination with the various additional treatments and techniques that are described in U.S. Pat. No. 5,928,239.

The illustrated embodiments are only examples of the present invention and, therefore, are non-limitive. It is to be understood that many changes in the particular structure, materials and features of the invention may be made without departing from the spirit and scope of the invention. Therefore, it is my intention that my patent rights not be limited by the particular embodiments illustrated and described herein, but rather determined by the following claims, interpreted according to accepted doctrines of claim interpretation, including use of the doctrine of equivalents and reversal of parts.

What is claimed is:

1. Apparatus for percutaneously forming an internal cavity in a body part, comprising:

a cavity cutting bit having an elongated shaft having an axis of rotation and a forward end;

a cutting tip member having a cutting end and a mounting end;

a hinge connecting the mounting end of the cutting tip member to the forward end of the elongated shaft, for free rotation of the cutting tip member relative to the shaft between a position in which the cutting tip member is coaxial with the shaft and a position in which the cutting tip member extends at an angle from the shaft;

a cutting-bit guide member having a forward end surface that is adapted to be placed against an outer surface region on a body part and a guide passageway that is adapted to receive the cutting tip member and the shaft, in that order;

an abutment on the shaft spaced a predetermined distance rearwardly from the cutting tip member; and a stop member spaced rearwardly of the forward end surface of the guide member and having a stop surface that is at a predetermined fixed position relative to the forward end surface of the guide member, the guide member extending forwardly from the stop member, wherein the forward end surface of the guide member can be placed against the outer surface region of the body part and the cutting tip member and shaft can be inserted into the guide passageway and moved into the body part to where a cavity is to be formed, and the shaft can be moved endwise until the abutment is against the stop surface, and the shaft can be rotated to cause the cutting tip member to swing outwardly and form the cavity, and wherein movement of the abutment against the stop surface prevents further endwise movement of the cutting tip member and establishes a predetermined end boundary for the cavity.

2. The apparatus of claim 1, wherein the stop member is between the abutment and the forward end surface of the cutting-bit guide member.

3. Apparatus for percutaneously forming an internal cavity in a body part, comprising:

a cavity cutting bit having an elongated shaft having an axis of rotation and a forward end;

a cutting tip member having a cutting end and a mounting end;

a hinge connecting the mounting end of the cutting tip member to the forward end of the elongated shaft, for free rotation of the cutting tip member relative to the shaft between a position in which the cutting tip member is coaxial with the shaft and a position in which the cutting tip member extends at an angle from the shaft;

a cutting-bit guide member having a forward end surface that is adapted to be placed against an outer surface region on a body part and a guide passageway that is adapted to receive the cutting tip member and the shaft, in that order;

an abutment on the shaft spaced a predetermined distance rearwardly from the cutting tip member; and a stop member having a stop surface that is at a predetermined fixed position relative to the forward end surface of the guide member, wherein the forward end surface of the guide member can be placed against the outer surface region of the body part and the cutting tip member and shaft can be inserted into the guide passageway and moved into the body part to where a cavity is to be formed, and the shaft can be moved endwise until the abutment is against the stop surface, and the shaft can be rotated to cause the cutting tip member to swing outwardly and form the cavity, and wherein movement of the abutment against the stop surface prevents further endwise movement of the cutting tip member and establishes a predetermined end boundary for the cavity;

wherein the abutment is forwardly of the stop member and the stop surface.

4. Apparatus for percutaneously forming an internal cavity in a body part, comprising:

a cavity cutting bit having an elongated shaft having an axis of rotation and a forward end;

a cutting tip member having a cutting end and a mounting end;

a hinge connecting the mounting end of the cutting tip member to the forward end of the elongated shaft, for free rotation of the cutting tip member relative to the shaft between a position in which the cutting tip member is coaxial with the shaft and a position in which the cutting tip member extends at an angle from the shaft;

a cutting-bit guide member having a forward end surface that is adapted to be placed against an outer surface region on a body part and a guide passageway that is adapted to receive the cutting tip member and the shaft, in that order;

an abutment on the shaft spaced a predetermined distance rearwardly from the cutting tip member; and a stop member having a stop surface that is at a predetermined fixed position relative to the forward end surface of the guide member, wherein the forward end surface of the guide member can be placed against the outer surface region of the body part and the cutting tip member and shaft can be inserted into the guide passageway and moved into the body part to where a cavity is to be formed, and the shaft can be moved endwise until the abutment is against the stop surface, and the shaft can be rotated to cause the cutting tip member to swing outwardly and form the cavity, and wherein movement of the abutment against the stop surface prevents further endwise movement of the cutting tip member and establishes a predetermined end boundary for the cavity;

wherein the stop member is a first stop member, and the apparatus further comprises a second stop member, each said stop member having a stop surface; and wherein the abutment on the shaft is between the two stop surfaces, and movement of the abutment against one of the stop surfaces establishes a first end boundary for the cavity being formed during rotation of the cutting bit and movement of the abutment against the other stop surface establishes a second, opposite end boundary for the cavity.

5. Apparatus for percutaneously forming an internal cavity in a body part, comprising:

a cavity cutting bit having an elongated shaft having an axis of rotation and a forward end;

a cutting tip member having a cutting end and a mounting end;

a hinge connecting the mounting end of the cutting tip member to the forward end of the elongated shaft, for free rotation of the cutting tip member relative to the shaft between a position in which the cutting tip member is coaxial with the shaft and a position in which the cutting tip member extends at an angle from the shaft;

a cutting-bit guide member having a forward end surface that is adapted to be placed against an outer surface region on a body part and a guide passageway that is adapted to receive the cutting tip member and the shaft, in that order;

an abutment on the shaft spaced a predetermined distance rearwardly from the cutting tip member; and a stop member having a stop surface that is at a predetermined fixed position relative to the forward end surface of the guide member, wherein the forward end surface of the guide member can be placed against the outer surface region of the body part and the cutting tip member and shaft can be inserted into the guide passageway and moved into the body part to where a cavity is to be formed, and the shaft can be moved endwise until the abutment is against the stop surface, and the shaft can be rotated to cause the cutting tip member to swing outwardly and form the cavity, and wherein movement of the abutment against the stop surface prevents further endwise movement of the cutting tip member and establishes a predetermined end boundary for the cavity;

wherein the guide member projects forwardly from said stop member and is adjustable in length for changing the distance between the stop surface and the forward end surface of the guide member.

6. The apparatus of claim 5, wherein the stop member is a first stop member, and the apparatus further comprises a second stop member, each said stop member having a stop surface; and wherein the abutment on the shaft is positioned between the two stop surfaces, movement of the abutment in a first direction against one of the stop surfaces establishes a first end boundary for the cavity and movement of the abutment in the opposite direction against the other stop surface establishes a second, opposite end boundary for the cavity, and the guide member is adjustable in length for changing the spacing of its forward end surface from each of the stop surfaces.

7. The apparatus of claim 6, wherein each stop member is adjustable relative to the other for changing the distance between the two stop surfaces.

8. Apparatus for percutaneously forming an internal cavity in a body part, comprising:

a cavity cutting bit having an elongated shaft having an axis of rotation and a forward end;

a cutting tip member having a cutting end and a mounting end;

a hinge connecting the mounting end of the cutting tip member to the forward end of the elongated shaft, for free rotation of the cutting tip member relative to the shaft between a position in which the cutting tip member is coaxial with the shaft and a position in which the cutting tip member extends at an angle from the shaft;

a cutting-bit guide member having a forward end surface that is adapted to be placed against an outer surface region on a body part and a guide passageway that is adapted to receive the cutting tip member and the shaft, in that order;

an abutment on the shaft spaced a predetermined distance rearwardly from the cutting tip member; and a stop member having a stop surface that is at a predetermined fixed position relative to the forward end surface of the guide member, wherein the forward end surface of the guide member can be placed against the outer surface region of the body part and the cutting tip member and shaft can be inserted into the guide passageway and moved into the body part to where a cavity is to be formed, and the shaft can be moved endwise until the abutment is against the stop surface, and the shaft can be rotated to cause the cutting tip member to swing outwardly and form the cavity, and wherein movement of the abutment against the stop surface prevents further endwise movement of the cutting tip member and establishes a predetermined end boundary for the cavity;

wherein the stop member extends substantially perpendicularly from an elongated base member.

9. Apparatus for percutaneously forming an internal cavity in a body part, comprising:

a cavity cutting bit having an elongated shaft having an axis of rotation and a forward end;

a cutting tip member having a cutting end and a mounting end;

a hinge connecting the mounting end of the cutting tip member to the forward end of the elongated shaft, for free rotation of the cutting tip member relative to the shaft between a position in which the cutting tip member is coaxial with the shaft and a position in which the cutting tip member extends at an angle from the shaft;

a cutting-bit guide member having a forward end surface that is adapted to be placed against an outer surface region on a body part and a guide passageway that is adapted to receive the cutting tip member and the shaft, in that order;

an abutment on the shaft spaced a predetermined distance rearwardly from the cutting tip member; and a stop member having a stop surface that is at a predetermined fixed position relative to the forward end surface of the guide member, wherein the forward end surface of the guide member can be placed against the outer surface region of the body part and the cutting tip member and shaft can be inserted into the guide passageway and moved into the body part to where a cavity is to be formed, and the shaft can be moved endwise until the abutment is against the stop surface, and the shaft can be rotated to cause the cutting tip member to swing outwardly and form the cavity, and wherein movement: of the abutment against the stop surface prevents further endwise movement of the cutting tip member and establishes a predetermined end boundary for the cavity;

comprising a longitudinal frame member; wherein said stop member is connected to and extends upwardly from and perpendicular to the longitudinal frame member, said stop member including a shaft receiving opening, and wherein the cutting-bit guide member projects forwardly from the stop member and the guide passageway in said cutting-bit guide member extends forwardly from the opening in the stop member.

10. The apparatus of claim 9, further comprising a handle connected to the longitudinal frame member, said handle projecting from said frame member in a direction opposite the stop member.

11. The apparatus of claim 9, wherein the stop member is a first stop member, and the apparatus further comprises a second stop member extending upwardly from and perpendicular to the longitudinal frame member, at a location rearwardly from the first stop member, said second stop member including a shaft receiving opening that is in alignment with the shaft receiving opening in the first stop member; and wherein the cutting tip member and a forward portion of the shaft extend forwardly through the opening in the first stop member and through the cutting-bit guide member and a rearward portion of the shaft projects rearwardly through the opening in the second stop member, and the abutment on the shaft is positioned between the two stop members.

12. The apparatus of claim 11, further comprising a handle connected to the longitudinal frame member, said handle projecting downwardly from said longitudinal frame member.

13. The apparatus of claim 11, comprising a base member on said longitudinal frame member, wherein said second stop member is connected to said base member and extends upwardly from and perpendicular to the base member, and wherein the base member includes a threaded upper portion having external threads, and said apparatus includes a ring that surrounds the base member and the longitudinal frame member and includes internal threads mating with the threads on the base member, and wherein rotation of the ring will cause the base member and the second stop member to move along the longitudinal frame member.

14. The apparatus of claim 13, further comprising a handle connected to the longitudinal frame member, said handle projecting downwardly from the longitudinal frame member.

15. A surgical method for percutaneous formation of a cavity within a body part, comprising the steps of:
 a) providing a percutaneous access opening into the body part;
 b) providing a stop member spaced outwardly from the access opening, and said stop member with a shaft receiving opening;
 c) inserting through the shaft receiving opening and through the access opening a rotary cavitation device comprising:
  i) an elongated shaft having a radius and an axis of rotation;
  ii) a cutting tip member having a fixed length;
  iii) a hinge interconnecting the shaft and the cutting tip member and allowing a free swinging movement of the cutting tip member between a first position in which the cutting tip member is coaxial with the shaft and a second position in which the cutting tip member extends outwardly at an angle from the shaft; and
  iv) an abutment on the shaft;
 d) positioning the abutment and the stop member such that when the shaft is moved axially to place the abutment into contact with the stop member the cutting tip member is positioned at an end boundary of the cavity that is to be formed in the body part;
 e) rotating the shaft at a velocity sufficient to cause the cutting tip member to swing from its first position into its second position and moving said cutting tip member to form an internal cavity in the body part and provide such cavity with a radius that is greater than the radius of the shaft; and
 f) withdrawing the shaft and the cutting tip member from the access opening.

16. The method of claim 15, comprising positioning the stop member forwardly of the abutment and moving the shaft axially forwardly to place the abutment into contact with the stop member and move the cutting tip member to an inner end boundary of the internal cavity that is to be formed in the body part.

17. The method of claim 15, comprising positioning the stop member rearwardly of the abutment and pulling the shaft rearwardly to move the abutment against the stop member and move the cutting tip member to an outer end boundary of the internal cavity that is being formed in the body part.

18. The method of claim 15, comprising providing a second stop member spaced outwardly from the abutment on the shaft, so that the abutment on the shaft is positioned between the two stop members, and positioning the second stop member at such a location that when the shaft is retracted to move the abutment into contact with the second stop member the cutting tip member is at a second, opposite end boundary of the cavity that is being formed.

19. The method of claim 15, comprising providing the stop member with a forwardly projecting guide tube with a front end surface that is positionable against a surface portion of the body part that is outwardly of where the cavity is to be formed and a guide passageway for the rotary cavitation device that is in alignment with the shaft receiving opening in the stop member, and extending said cutting tip member forwardly into and through the guide passageway and into and through the access opening into the body part and then rotating the cutting tip member to form the cavity.

20. The method of claim 19, comprising positioning the abutment and the stop member by adjusting the length of the guide tube.

21. The method of claim 20, comprising providing a second stop member spaced outwardly from the abutment on the shaft so that the abutment on the shaft is positioned between the two stop members, and positioning the second stop member at such a location that when the shaft is retracted to move the abutment into contact with the second stop member the cutting tip member is at a second, opposite end boundary of the cavity that is being formed.

22. The method of claim 21, comprising positioning the second stop member by moving it in position relative to the front end surface of the guide tube.

23. The method of claim 15, wherein the stop member is a first stop member, and the method comprises providing a second stop member spaced outwardly from the abutment on the shaft, so that the abutment on the shaft is positioned between the two stop members, mounting the second stop member on a longitudinal base member that includes lead screw threads; positioning the base member on a longitudinal frame member that is connected to the first stop member; and providing an adjustment ring that surrounds the base member and the frame member and includes internal threads that engage the lead screw threads on the base member, and rotating the ring for causing movement of the base member and the second stop member relative to the first stop member.

24. The method of claim 23, comprising providing the first stop member with a forwardly projecting guide tube with a front end surface that is positionable against a surface portion of the body part that is outwardly of where the cavity is to be formed, and a guide passageway for the rotary cavitation device that is in alignment with the shaft receiving opening in the stop member, and extending the cutting tip member and a forward portion of the shaft through the guide passageway, and positioning the abutment and the stop member by adjusting the length of the guide tube so as to change the positioning of the abutment and the stop member from the front end surface of the guide tube.

* * * * *